United States Patent [19]

Meyer et al.

[11] Patent Number: 4,976,949

[45] Date of Patent: Dec. 11, 1990

[54] CONTROLLED RELEASE DOSAGE FORM

[75] Inventors: James H. Meyer, Santa Monica, Calif.; Gordon L. Amidon; Jennifer B. Dressman, both of Ann Arbor, Mich.

[73] Assignee: The University of Michigan, Ann Arbor, Mich.

[21] Appl. No.: 474,633

[22] Filed: Jan. 29, 1990

Related U.S. Application Data

[63] Continuation of Ser. No. 791,586, Oct. 25, 1985, abandoned.

[51] Int. Cl.$^5$ .......................... A61K 9/22; G01N 37/00
[52] U.S. Cl. ...................................... 424/1.1; 424/468; 424/497; 436/56
[58] Field of Search .................... 424/1.1, 9, 468, 497; 436/56

[56] References Cited

U.S. PATENT DOCUMENTS 4,115,540  9/1978  Digenis et al. ........................ 424/1.1
4,193,985  3/1980  Bechgaard et al. ................... 424/19

FOREIGN PATENT DOCUMENTS 1509866  5/1978  United Kingdom .
1561613  2/1980  United Kingdom .

OTHER PUBLICATIONS

Dressman & Amidon, J. of Pharmaceutical Sciences, vol. 73, No. 7, pp. 935 to 938, Jul. 1984.

Primary Examiner—John S. Maples
Attorney, Agent, or Firm—Rohm & Monsanto

[57] ABSTRACT

A dosage system for administering drugs and conducting gastric flow studies is configured in the form of a multiplicity of substantially spherical subunits which have advantageously preselected particle diameter and density to customize the flow rate of the subunits with respect to the rate of flow of at least certain portions of the chyme. The diameter and density are related to one another in accordance with a relationship:

$$N_v = \frac{g \Delta p \cdot d_p^2}{\mu \cdot <v>}$$

where $N_V$ is a dimensionless group having a predetermined value representing gastric residence time, g is the gravitational constant, $\Delta p$ is the difference in density between the subunits and the chyme, and $<v>$ is the linear velocity of the chyme. The flow rate of the subunits can be made slower, faster, or substantially equal to that of the chyme, as required to treat certain disease states. Also, the subunits can be provided with an enteric coating which permits more precise administration of certain drugs, such as those used in enzyme supplementation therapy. This is particularly useful in treating patients with abnormal duodenal pH levels, such as are encountered in victims of cystic fibrosis and other forms of pancreatic insufficiency.

19 Claims, 4 Drawing Sheets

CONTROLLED RELEASE DOSAGE FORM

This invention is subject to a reservation in the Government of a nonexclusive, irrevocable, royalty-free license in the invention with power to grant licenses for all governmental purposes.

This application is a continuation, of application Ser. No. 791,586, filed Oct. 25, 1985, now abandoned.

BACKGROUND OF THE INVENTION

This invention relates generally to controlled release multiple subunit drug dosage forms, and more particularly to a controlled release drug dosage form which can be adapted for delivery of the drug to the upper gastrointestinal tract concomitantly with the emptying of a meal.

In the treatment of a mammal with a drug it is often desirable to control delivery of the active drug to the intestine of the mammal so as to avoid inactivation of the drug by exposure to gastric pH levels. Moreover, such controlled delivery is useful to avoid irritation of the gastrointestinal mucosa, to control the amount of active drug delivered at a given time, and to increase upper gastrointestinal residence time. It is additionally desirable to maximize contact time of a drug with a meal and the substances secreted in response to the meal. Such control over contact time is especially desirable in exogenous enzyme replacement therapy.

Various techniques and devices are available in the art to control the delivery of an active drug to the duodenum. One such technique utilizes an enteric coating over the dosage form which contains the drug. The enteric coating protects the coated dosage form from dissolution at low gastric pH levels. A further technique involves administration of a dosage from insoluble drug permeable matrices such as waxes, polymers, or ion exchange resins of types which are known in the art. These known dosage forms are plagued with a variety of disadvantages. For example, nondisintegrating forms may cause obstruction in patients with impaired motility. Also, ion exchange resins do not provide complete release of the drug, thereby resulting in wastage of the drug and uncertainty as to the dosage amount.

Certain disease states, such as cystic fibrosis and chronic alcoholism, are characterized by pancreatic insufficiency. Exogenous enzyme replacement is frequently indicated, but there has been a need in the art for a dosage form which will travel concurrent with an ingested meal and release active enzymes in the duodenum in order to approximate the activity of a healthy pancreas. The pancreas normally produces a secretion, which passes through the pancreatic duct into the duodenum and which is essential to the digestion process. The pancreatic secretion contains enzymes such as amylases, lipases, and proteases, the loss of which results in intestinal malabsorption of fats, proteins, and, to a lesser extent carbohydrates. Symptoms of pancreatic insufficiency include abdominal distention, steatorrhea, creatorrhea, rectal prolapse, deficiencies of fat soluble vitamins (A,D,E, and K), hypoproteinemia, anemia, and hypoprothrombinemia.

The primary treatment for pancreatic insufficiency is therefore pancreatic enzyme supplementation, which reduces the amounts of fat and nitrogen excreted unabsorbed. However, the amounts of fat and nitrogen in the stool are only rarely reduced to normal levels at least partially as a result of inactivation of the enzymes by gastric acidity. It is known, however, that other factors are involved since therapy with histamine $H_2$-receptor antagonists or antacids, administered concomitant with the enzymes, does not result in a normalization of digestion.

Since pancreatic enzymes are inactivated at gastric pH levels, enteric coatings are commonly utilized to protect the enzymes until they reach the duodenum. Preferably, such a dosage form will release the enzymes in about 5 to 30 minutes since digestion and absorption of metabolites occurs primarily in the upper segment of the intestine, i.e., the duodenum and jejunum. Thus, duodenal pH is a key factor in determining the rapidity with which the formulation releases the enzymes. The more rapidly the enzymes are released, the greater the length of intestine over which the enzymes are available to digest the meal. This leads to better absorption of nutrients from the ingested meal and thereby avoids the undesirable effects listed above which result from large quantities of undigested meal components reaching the colon. However, there is a problem with such enteric coating in that acidic conditions in the duodenum will delay dissolution of the enteric coating, thereby delaying enzyme release until the intestinal contents reach a more distal segment of the intestine with a higher pH. This delay effectively reduces the time during which enzymatic digestion can occur before the meal passes into the colon.

Enteric coatings in commonly used formulations take anywhere from 15 minutes to two hours to dissolve after gastric emptying in normal subjects. Any additional delay resulting from low duodenal pH, as is the case with those suffering from cystic fibrosis, would be expected to compromise the efficacy of the enzymes substantially.

Prior art techniques to deliver drugs such as pancreatin to the duodenum, and thus maximize contact time with the meal and substances secreted in response thereto, include devices of the type disclosed in British Patent No. 1,561,613. This patent describes a dosage unit comprising pancreatin, a distending agent which will exert an osmotic pressure when in aqueous solution, and a basic material contained in a sealed polymeric, semi-permeable film which is resistant to attack by gastric juice. This dosage unit swells in response to the gastric juice. However, the pancreatin is protected from becoming inactivated by operation of the basic material which neutralizes the effects of the gastric juice on the pancreatin. The British patent further teaches that this known dosage form is mechanically ruptured when it is in the region of the pyloric sphincter. It is evident that this known dosage form suffers from an inability to dispense the drug continually, but rather releases the drug all at once when the rupture occurs.

A further known technique is described in British Patent No. 1,509,866 and utilizes a gastric juice soluble capsule having multiple subunits therein which are controlled as to particle size diameter and coated with an enteric coating which dissolves at neutral to alkaline pH levels. The diameters specified in this patent range from about 1.68 to 2.38 mm. Suitable enteric coatings are specified in this patent to include cellulose acetate phthalate plasticized with diethyl phthalate. It is a significant disadvantage of this known dosage form that the high pH-dissolving coating limits the contact time of the pancreatin with the meal. Furthermore, it will be shown hereinbelow that the size and density combinations disclosed in this British patent will result in the drug being emptied at a rate slower than the meal.

It should be noted that exogenous administration of enzymes in large tablets can aggravate the existing physiological condition because large doses of enzymes are released in a small concentrated area resulting in irritation and damage to the intestinal lining and abnormal distribution of enzymes. Moreover, any asynchrony that might exist between the arrival of food and the tablet from the stomach into the duodenum will further reduce the possibility that normal digestion will take place. Non-concomitant arrival of the enzymes with respect to the food results in unpredictable response and poor digestion.

It is evident from the foregoing that significant problems exist in the present state of the art of preparing a suitable drug form for pancreatic enzyme supplementation. For example, there is a need for a proper enteric coating which will ensure delivery of the drug into the duodenum. Additionally, there is a need for a dosage form which releases the enzymes in a biologically active state, and which recreates the conditions of normal pancreatic function. To date, however, pancreatic enzyme supplementation dosages are not available which can be adapted to deliver a drug concomitantly with a meal.

It is to be understood that the treatment of certain disease states by dosage systems which operate concomitantly with a meal represents only one desired, but unachieved, goal in the prior art. Some diseases could be treated effectively by use of dosage systems which deliver an active drug either prior to, or after, emptying of a meal, if such dosage forms were available. Thus, there is a need for a dosage system wherein the time of delivery of an active drug, with respect to the time of ingestion of a meal, can advantageously be selected.

In addition, there is a need for a dosage form for concomitant delivery of a marker with respect to a meal for gastric emptying studies. Currently used markers, such as In-DPTA complexes, measure only the emptying rate of the liquid fraction of the gastric contents, and it is often desired to measure the emptying rate of the solid fraction. Radiolabeled filter paper squares have been used, but are suspected of emptying slower than the meal, and are therefore unreliable as a marker. Gamma-labeled test meals have been used, but extracellularly labeled meals may disadvantageously be subject to gamma label dissociation from the meal into the liquid fraction, thereby rendering this type of marker inaccurate, and intracellularly labeled meals have the disadvantage of being difficult to prepare.

Accordingly, it is an object of the invention to provide a controlled release dosage form having an increased gastric residence time.

It is another object of the invention to provide a controlled release dosage form which can be delivered at the same rate as a meal.

It is further an object of the invention to provide a controlled release dosage form which can be adapted simply, such as by particle size and density combinations, to any desired emptying pattern.

It is also an object of the invention to provide a controlled release dosage form wherein an enteric coating is tailored to the individual pH profile of the gastrointestinal tract of an individual or of a representative sample of individuals in the diseased state.

It is an additional object of the invention to provide a controlled release pancreatic enzyme supplementation system which approximates the conditions of normal digestion.

It is still another object of the invention to provide a marker for studying meal emptying rate which will accurately measure motility functions in the fed state.

It is also another object of the invention to provide a controlled release dosage form which will uniformly dispense throughout the meal.

It is a still further object of the invention to provide a dosage form which will control delivery of the drug to the intestine to increase upper gastrointestinal residence time, avoid irritation of the gastrointestinal mucosa, and/or avoid precipitation of the drug in the bowel.

It is yet an additional object of the invention to provide a dosage form which maximizes contact time of the drug with the meal and with substances secreted in response to the meal.

It is additionally an object of the invention to provide a method of manufacturing a drug which is customized to travel at a predetermined rate with respect to a meal, and to dissolve at a predetermined point within the gastrointestinal tract.

SUMMARY OF THE INVENTION

The foregoing and other objects are achieved by this invention which provides a drug dosage system of the type wherein an active drug is administered orally to a living being so as to be transported by chyme produced by the living being in response to an ingested meal. The drug is arranged in a multiplicity of subunits, each of which has a substantially spherical configuration and a predeterminable density and diameter. The density and diameter are related to one another in accordance with the relationship:

$$N_v = \frac{g\Delta p \cdot d_p^2}{\mu \cdot <v>},$$

in which $N_v$ is functionally related to the gastric residence time relative to the liquid portion of the meal; g is the gravitational constant; $\Delta p$ is the difference in density between the subunits and the chyme; $d_p$ is the diameter of the subunits; $\mu$ is the viscosity of the chyme; and $<v>$ is the linear velocity of the chyme.

In a practical embodiment of the invention, the density of the subunits is selected to be approximately between 0.5 and 2.0 g/ml. Additionally, the diameter of the subunits is selected to be approximately between 0.5 and 2.5 mm. Furthermore, the density and size combination should be $|\Delta p| \cdot d_p^2 \leq 2.5$ for concomitant emptying. Such a dosage system is particularly adaptable for the delivery of a digestive enzyme, such as pancreatin.

In addition to controlling the size and density of a subunit of the drug, additional control over the time at which the drug is released, and the location along the gastrointestinal tract where such release is effected, can be achieved by use of an enteric coating. The particular characteristic of the selected enteric coating may be responsive to predetermined gastrointestinal conditions of the living being to which the drug is to be administered. For example, such gastric conditions may be predetermined for selected disease states. In an illustrative embodiment of the invention which is adapted for treatment of cystic fibrosis, the enteric coating can be selected to dissolve when subjected to a pH range of approximately between 4.5 and 5.5. Alternatively, the gastrointestinal conditions for which the drug dosage form is adapted may correspond to normal gastric pH profiles.

As will be discussed hereinbelow, the present invention is suitable for conducting gastrointestinal studies and experiments. During such studies, it is desirable to radiolabel the subunits to facilitate their detection after emptying. Therefore, the present invention is not limited to the administration of active drugs, but also may be applied in the administration of indigestible subunits, illustratively formed of plastic materials, for conducting studies and experimentation.

In accordance with a method aspect of the invention, the subject dosage form is formed by predetermining a density of the chyme produced by a living human being in response to an ingested meal, predetermining a viscosity of the chyme, predetermining a linear viscosity of the chyme, and determining a density and diameter of the subunits in accordance with the mathematical relationship noted hereinabove. In embodiments where it is desired that the subunits empty substantially concomitantly with the meal, the density and diameter of the subunits are selected so as to produce substantially the same value of $N_v$ as the solid fraction of the meal. In certain embodiments, the density and diameter values are selected such that the relationship: $|\Delta p| \cdot d_p^2$ is within the range of approximately 0 to 20.5 when density is given in terms of g/ml and diameter is given in mm. The density and diameter values thus selected are particularly useful in the delivery of digestive enzymes.

BRIEF DESCRIPTION OF THE DRAWING

Comprehension of the invention is facilitated by reading the following detailed description in conjunction with the annexed drawing in which.

DETAILED DESCRIPTION OF THE INVENTION

The present invention provides a controlled release dosage form of the type which comprises microspherules or multiple subunits containing an active drug. Control of the diameter and density of the spherules enables control of the gastric emptying pattern of the spherules with respect to the gastric emptying pattern of a meal as will be discussed hereinbelow.

In a particularly advantageous embodiment of the invention, the drug dosage form can be adapted to deliver the drug at the same rate as the meal. Concomitant emptying of a drug and an ingested meal maximizes the contact of the drug with the meal and the secretions of the gastrointestinal system produced in response to the meal. This is particularly important in applications such as pancreatic enzyme replacement therapy, delivery of bicarbonate to the small intestine to correct acidosis in the lumen, duodenal delivery of bile salts to enhance absorption of fat soluble vitamins and essential fatty acids in biliary atresion or other obstructions of the biliary tract, and the prevention of absorption of ingested nutrients which are present in the body in clinically excessive amounts.

Ingested food leaves the stomach primarily as particles having a maximum dimension of less than about 1 to 2 mm. Experimental results in a canine model indicate that nondigestible particles having a diameter greater than about 5 mm do not leave the stomach when food is present. Spherules of drug which are not dissolvable at gastric pH would act as "nondigestible particles." This so-called seiving action of the antropyloric segment appears to be a functional process rather than an anatomical process since it appears to be based on muscular pumping action and fluid flow rather than the size of the pyloric opening. It is therefore postulated that gastric emptying of drug spherules is governed essentially by the principles of hydrodynamics over the particle size range of practical interest (microspherule diameter, as limited by the ability to manufacture, and the maximum diameter of the lumen of the pylorus). The application of dimensional analysis shows that particle size and density of the drug spherules are key parameters, and are related on one another in accordance with the following formula:

$$N_v = \frac{g \Delta p \cdot d_p^2}{\mu \cdot <v>} \qquad \text{(Eqn. 1)}$$

wherein $N_v$ is functionally related to the gastric residence time relative to the liquid fraction of the meal; g is the gravitational constant $\Delta p$ is the density difference between the spherules and fluid $(p_2-p_1)$; $d_p$ is the particle diameter in mm; $\mu$ is the viscosity of the fluid; and $<v>$ is the linear velocity of the fluid.

$N_v$ is a relative measure of the emptying rate of particles of an ingested meal relative to the fluid and of the emptying rate of drug spherules relative to the fluid. The "fluid" consists of the mixture of food and endogenous gastric secretions known as chyme which empties from the stomach into the duodenum. Viscosity, density, and linear velocity are meal content dependent, but any change in flow rate (or linear velocity) and/or viscosity in any given meal would affect the meal particles and the drug spherules to a similar extent. Thus, the absolute value of $\Delta p \cdot d_p^2$ is the most important factor. A density difference of zero leads to emptying of particles with the fluid fraction of the meal. Other density differences result in emptying rates slower than the fluid. In certain ranges of $|\Delta p| \cdot d_p^2$ the particles empty slower than the fluid, but concomitant with the solid fraction, which is the fraction of interest. As used herein, concomitant emptying shall mean the rate of emptying of the solid fraction of the meal ±20%.

The density of chyme approximates 1 g/ml. There is published data available concerning flow rate and viscosity. Moreover, persons of skill in the art can measure these parameters by known techniques if desired.

In order to study the particle size and density relationship, gastric emptying of indigestible particles in dogs was investigated as follows:

Six mongrel male and female dogs, weighing 40 to 60 lbs, with chronic duodenal fistulae were fasted at least 18 hours prior to the experiment. Each dog was fed a test meal consisting of 70 g of beefsteak and 30 g $^{99m}$Tc-labeled liver cut into 1 cm cubes. Immediately after eating the test meal, the dog was administered approximately 5 g, or 50–100 particles, via an orgastric tube which was inserted for this purpose. The particles were of the following diameters: 15μ, 1.2 mm, 1.6 mm, 2.4 mm, 3.2 mm. and 5 mm. The particles were administered together with 60 ml of water to ensure their complete and immediate delivery to the stomach. Table I lists the particle sizes, densities, and types of material used in the gastric emptying studies.

TABLE I

| Particle Size (Diam.) | Material |
| --- | --- |
| 15 microns | Polystyrene DVB labeled with $^{51}$Cr |
| 1.2 mm | Polystyrene DVB (Amberlite 430) $^{51}$Cr |
| 1.6 mm | Teflon ® (p = 2), nylon (p = 1) |
| 2.4 mm | Teflon ®, nylon |
| 3.2 mm | Teflon ®, nylon |
| 5.0 mm | Polypropylene (p = 1) |
| 2.4 mm | Polystyrene foam (p = 0.5) |

All material leaving the stomach was diverted through the duodenal fistula and collected at 15 minute intervals. Digesta exiting the duodenal cannula was collected over a stack of four sieves having respective mesh sizes of 0.5, 0.25, 0.125, and 0.063 mm. Sieve sizes were selected to retain particles having the diameters of interest, while allowing sufficient chyme to pass through to reinstill into the distal duodenum.

In cases where the administered particles had diameters of 1 mm or greater, the particles were recovered from the coarsest sieve and counted manually to determine the number emptied in a given 30 minute period. For smaller particle sizes, it was easier to use radiolabeled particles with $^{51}$Cr, for example, and then to determine the number emptied by gamma counting of the particles recovered from the appropriate sieve sizes.

The fine suspended material which passed through all of the sieves was kept homogenous, sampled for gamma counting, and returned to the distal duodenum via a Foley catheter, over the subsequent 15 minute interval. Reinstillation of the chyme was necessary to ensure that the gastric emptying rate remained within normal limits for the dog. Collections were made for five hours postprandially so that particle emptying over the entire meal emptying period could be determined.

Figure 1:
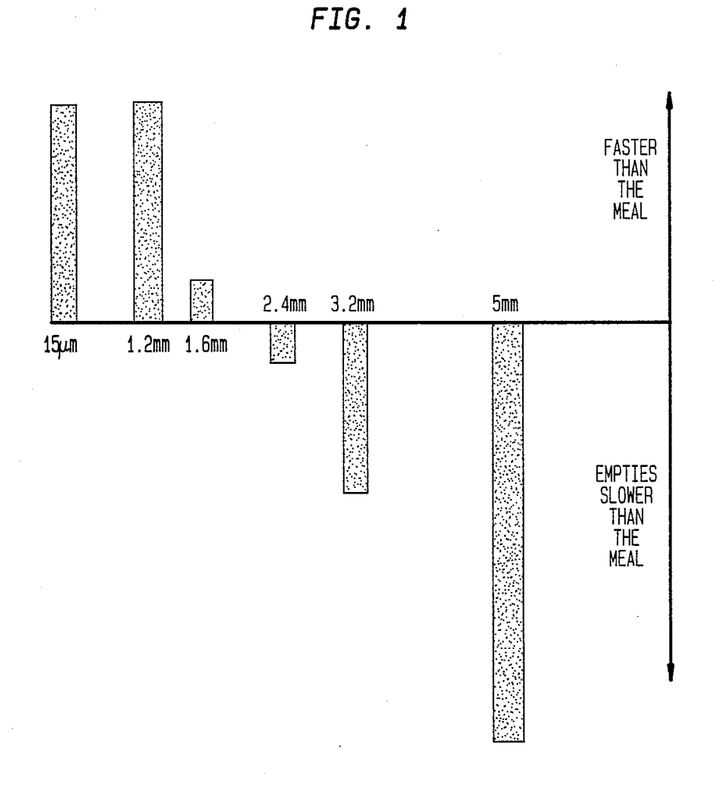
FIG. 1 is a bar graph which illustrates the emptying of spheres relative to a meal.
Figure 2:
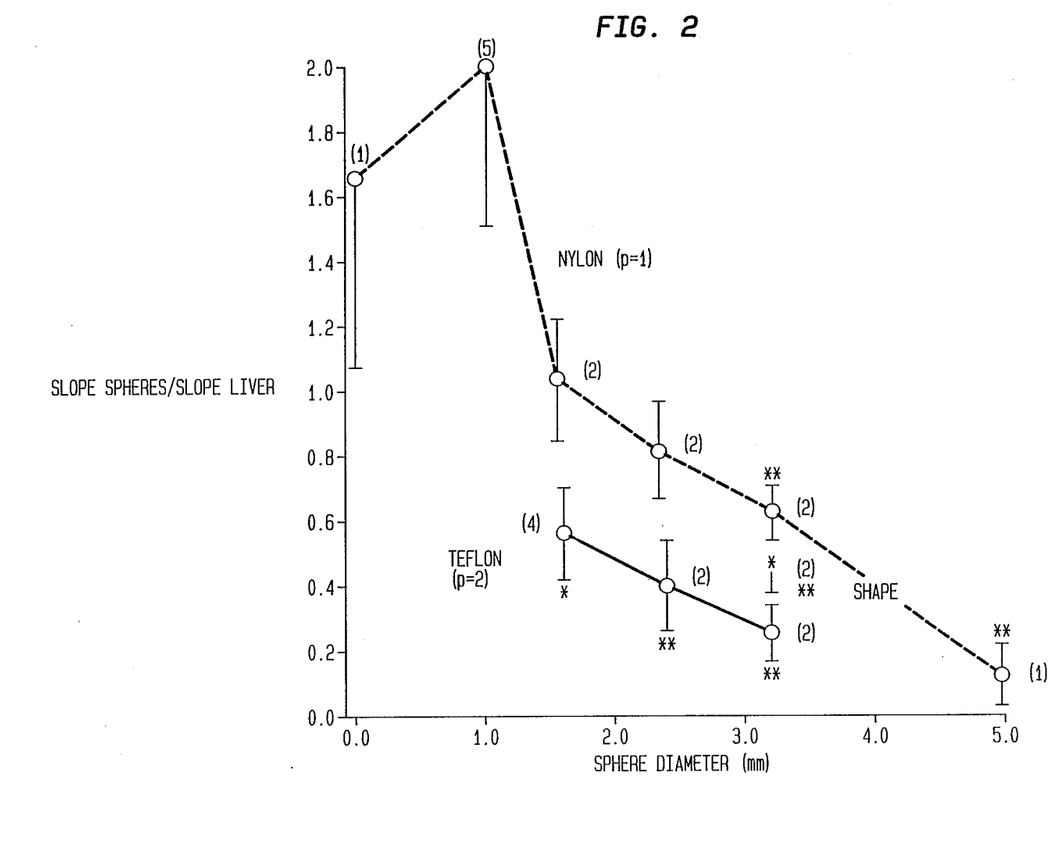
FIG. 2 is a graph which illustrates the effects of differences in density between the spheres and the chyme.

A summary of the results is shown in FIGS. 1 and 2 and in Table II below. From FIG. 1, it is apparent that for a dosage form of density 1 g/ml, a particle size of approximately 1.3 to 2.0 mm diameter is required for concomitant meal and particle emptying. As used herein with respect to the present invention, meal and particle emptying shall be deemed to be concomitant if their respective emptying rates are within 20% of one another.

At a density of 2 g/ml, the particle size required to achieve concomitant emptying drops to less than about 1 mm in diameter. The data depicted in the bar graph of FIG. 1 were obtained by first plotting (not shown) particle emptying against meal emptying, to normalize for day/day and dog/dog handling of the meal. If both emptied at equal rates, then the relation would be y=x. A positive deviation from this relationship indicates that the particles empty faster than the meal, while a negative deviation indicates a slower emptying rate for the particles relative to the meal. In FIG. 1, the signed sums of the deviations are plotted as a function of particle size, for particles of density approximately 1 g/ml. There is a dramatic change between faster and slower emptying of spheres versus the meal between a particle diameter of 1.6 and 2.4 mm.

TABLE II

Signed Sum Deviation From Concomitant Emptying With The Meals As A Function of Density

| | | Signed Sum Deviation | | |
| --- | --- | --- | --- | --- |
| | Density | 1.6 mm | 2.4 mm | 3.2 mm |
| With | 1 | +41 | −45 | −180 |
| 60 ml | 2 | −208 | −336 | −211 |
| Water | | | | |
| With | 1 | — | −163 | — |
| 180 ml | 0.5 | — | −337 | — |
| Water | | | | |

FIG. 2 is a graph which shows the effect of density difference between the spheres and the chyme. FIG. 2 and Table II indicates that for spheres which are either twice as dense or half as dense as the chyme, emptying is substantially slower than for spheres of similar density to the chyme. The effect appears to be most striking at particle sizes which result in an emptying pattern similar to that of the meal. Slope ratio values greater than 1 indicate that the particles empty faster than the meal. For particles of density equal to 1 g/ml (top curve), particles of 1.5 mm diameter empty in concert with the meal. Since concomitant emptying particle size ranges vary somewhat depending on the statistical analysis method used, a preferred range was established based on the combined results of the two methods used.

Further experiments were conducted in a similar manner to investigate the effects of flow rate of the chyme and the viscosity of the gastric contents on gastric emptying of the indigestible particles. In these experiments, 50 Teflon spheres having a density of 2 g/ml and a diameter of 3.2 mm were instilled through the orogastric tube, following ingestion of the test meal, with either 200 ml or 800 ml volumes of saline (0.15M NaCl, 1 centipoise) or saline/guar (1.33% guar polysaccharide, 2800 centipoise). The volume difference was used to create different rates of fluid outflow from the dog's stomach and the guar was used to create a density difference in the gastric content. Either volume was instilled quickly, and the particles being added to the orogastric tube after half of the planned volume had been added. The orogastric tube was removed and the gastric emptying was studied for three hours postprandially.

Fluid outflow was twice as fast after the 800 ml instillates (although four times the volume of the 200 ml instillates). The faster outflow did not increase the rate of particle emptying. Increasing the viscosity had little effect on the rate of liquid emptying from the stomach, but did increase the rate of emptying of the particles. It also significantly increased the diameter of emptied particles of the meal, indicating that viscosity affected meal and drug particle emptying to about the same degree.

The canine model is a good model with respect to human seiving characteristics. While the dog empties food at about one half the speed of a human, the size of food particles emptied are similar. Both human and dog will empty 0.35 mm particles with the fluid fraction of the meal, while retaining 5 mm particles. Thus, the relationship given by Eqn. (1), and verified through the canine studies, can be applied to the manufacture of a dosage form for selectably choosing the rate of emptying of drug, particles with respect to the emptying rate of a meal. In a preferred embodiment of the invention, the emptying rates are chosen to be approximately equal. Since most drugs of interest will have densities in the range of 0.5 to 2.0 g/ml; particle diameters will range from about 0.5 to 2.5 mm. More specifically, for a density on the order of 1 g/ml, particle size diameters will range from about 1.3 to 2.5 mm. For a particle density on the order of 2.0 g/ml, particle diameter will be approximately 0.5 to 1.5 mm. As discussed hereinabove, viscosity and flow rate of the chyme will affect the rate of emptying of the particles of drug by about the same amount as the particles of food in the chyme. Thus, a key factor is the absolute value of the density difference between the particles and the chyme multiplied by the diameter of the drug particles squared: $|(p_2-p_1)| \cdot d_p^2$. For concomitant emptying the value of this relationship ranges from 0 to 2.25.

In a preferred embodiment of the invention, the density of the drug formulation, including excipients, is predetermined and the particle size diameter is calculated according to Eqn. (1) depending upon the desired value of $N_v$ to produce the selected emptying pattern. Of course, the appropriate density can be calculated for any given particle size diameter. Density can be increased by incorporating a physiologically inert substance into the formulation of the drug. For example, the density-augmenting substance can be included in the core of the particle or in a coating material of the drug particles. Examples of substances which can be used to increase specific weight of the particulate drug spheres include sodium carbonate, barium sulphate, or zinc oxide.

In order to manufacture the particulate drug spheres of the instant invention, equipment is needed to produce coarse multiparticulates. Two commonly used pieces of equipment for this purpose are the centrifugal granulator and the Marumerizer.

A centrifugal granulator, such as the CF granulator manufactured by Freund Industrial Co., dist. by Vector Corp., Iowa, can be used as described in the following illustrative example. Powdered drug is agglomerated onto Nupareil (Ingredient Technology Corporation, Pennsauken, New Jersey) starter seed using a solution of binder materials, such as are known in the art. To obtain spherical particles, this process is carried out in a rotating vessel. After the spheres are formed, the spray solution can be changed to a coating solution of any desired type so that the spheres can be coated in situ. This procedure is most suitable for low dose drugs because the Nupareil starter seeds occupy a significant volume, thereby limiting the amount of drug which can be added while still retaining an acceptably sized product.

The Marumerizer technique involves blending the drug with a diluent, such as lactose, a binder, and in certain instances with a dispersant, such as Avicel (a type of microcrystalline cellulose) to form a paste. The paste is extruded through a screen of suitable mesh size. The extruded ribbons of paste are cut to approximate lengths and transferred to a spheronizing bowl where rapid centrifugal and frictional action causes the extruded pellets to assume a spherical shape. Thus, granules of regular size, shape, and surface characteristics are formed. After the spheres are formed and dried, they can be enteric coated, if desired, in a Uni-Glatt air suspension coater, or any other known fluidized bed equipment typically used in the pharmaceutical industry for coating operations. Parameters such as bed pressure, inlet temperature, flow rate of coating solution can all be closely controlled to assure a reproducible operation.

In a specific illustrative embodiment, a rotating pan apparatus was used to produce granules in the particle size range having the formula:

|  | (% by weight) |
|---|---|
| Pancreatin | 78 |
| Sodium Carbonate | 4 |
| Citric Acid | 3 |
| Avicel | 10 |
| PVP 40T | 5 |

All of the ingredients except PVP 40T were mixed in the rotating pan. The PVP was dissolved in isopropyl alcohol and sprayed onto the tumbling powder until a wet granulation was produced. The granulation was dried in an oven overnight and then sieved to obtain the appropriate size. In the above-referenced formula, sodium carbonate was added to increase the pH of the formulation and Avicel and PVP 40T (Polyvinyl pyrollidine) were used as binders. A sample of the produced pellets was subjected to simulated intestinal conditions and observed for dissolution. About 95% of the pellets dissolved within 15 minutes.

In yet another illustrative embodiment of the invention, the following formulation was granulated as described above:

|  | (% by weight) |
|---|---|
| Pancreatin | 75 |
| Sodium Bicarbonate | 10 |
| PVP 40T | 5 |
| Ac-Di-Sol | 3 |
| Salicylic Acid | 7 |

The salicylic acid was used as a marker for dissolution studies. Sodium bicarbonate can be replaced the carbonate to decrease the pH. Ac-Di-Sol swells on contact with gastrointestinal fluid to aid disintegration. Dissolution in simulated intestinal conditions took less than 5 minutes.

In a specific illustrative application of the principles of the invention, a drug dosage form for pancreatic enzyme supplementation or replacement therapy is utilized. In order to design a good enzyme dosage form, the emptying rate of the drug particles should be concomitant with the emptying rate of an ingested meal so as to maximize contact of the meal with the enzymes. Moreover, the particles should have an enteric coating to protect the enzymes against inactivation by gastric pH levels, but which dissolves in the upper gastrointestinal tract (e.g., the duodenum) within a short period of time.

As discussed above, we have discovered a relationship which enables calculation of the appropriate size and density of drug spherules for concomitant emptying. In addition to controlling the rate of transmission of the drug particles with respect to the rate of transmission of the meal, we control the site and time of delivery of the drug by the choice of the proper enteric coating. The choice of an enteric coating can be made by measuring the pH and time profile for an individual or for a representative sample of individuals in a particular state of health or disease, and then tailoring the enteric coating dissolution characteristics to ensure delivery of the active drug to the duodenum, or any other point in the gastrointestinal tract, as desired.

Figure 3:
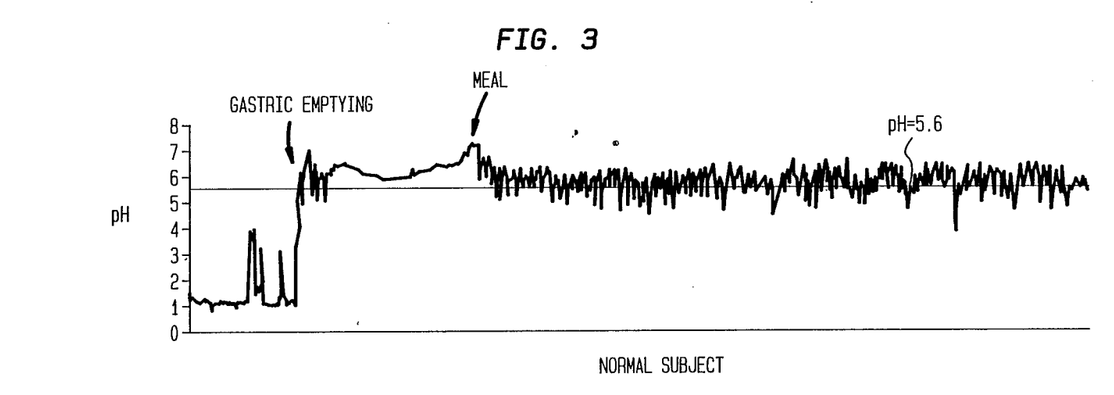
FIGS. 3 and 4 are graphs which illustrate typical postprandial pH profiles in the duodenums of normal and cystic fibrosis subjects, respectively.
Figure 4:
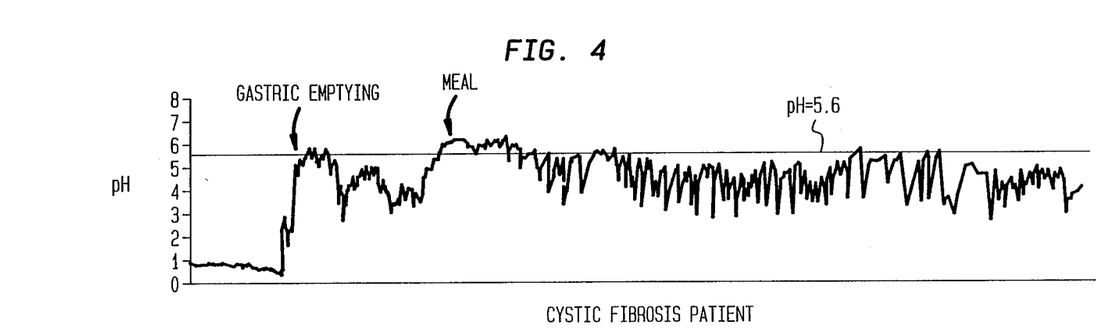

The fasted pH profiles of cystic fibrosis patients and healthy subjects show a similar gastric pH, but are significantly different in intestinal pH. In normal subjects, duodenal pH consistently reached 5.5 in the four hour postprandial period. In cystic fibrosis patients, the results varied, but the maximum pH ranged from about 4.5 to 5.5. FIGS. 3 and 4 show the typical postprandial pH profiles with respect to time for healthy subjects and cystic fibrosis patients, respectively.

The data on FIGS. 3 and 4 were obtained by continuously monitoring the pH with respect to time using a radiotelemetric device, the Heidleberg capsule. The Heidleberg capsule consists of a battery-powered high frequency radio transmitter and pH electrode housed in a nondigestible acrylic capsule of approximately 7 mm diameter and 20 mm length. The frequency of transmission changes with the pH of the capsule's environment and can be calibrated with standard buffer solutions. The test subject wears an antenna strapped around the midriff to receive the radio signal, which is converted back to pH and recorded as a function of time. The radiotelemetric test procedure is described more completely in an article by Dressman and Amidon, *Journal of Pharmaceutical Sciences*, Vol 73, No. 7, pages 935 to 938, July, 1984. Of course, other techniques known to those of skill in the art, such as gastrointestinal fluid aspiration, can be used to generate data concerning the pH profile.

Postprandial pH in the duodenum of cystic fibrosis patients followed a qualitatively similar pattern to that of healthy subjects, in that there was a tendency for pH to decrease with time and the pH fluctuated repeatedly after eating. However, in 8 of 10 healthy subjects, there was a rise of 0.5 to 1 pH unit in the duodenum as the subject started to eat. In one of the remaining two subjects, the pH was already greater than 7. In cystic fibrosis patients, the initial rise in duodenal pH in response to meal intake was absent in all but one profile. In addition, the mean pH profile was lower for cystic fibrosis patients than healthy subjects in any given hour. This trend was significant in the first hour both for time spent below pH 6.0 and 5.5.

Figure 5:
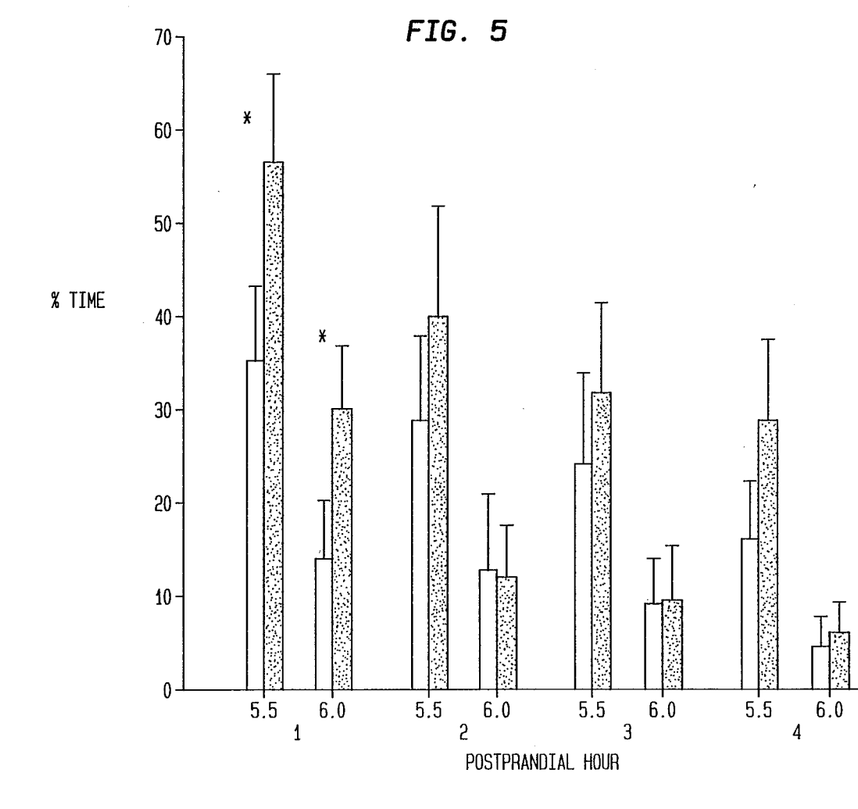
FIG. 5 is a bar graph which illustrates the percentage of time spent above pH 5.5 and pH 6.0 in each postprandial hour in the duodenum of healthy and cystic fibrosis subjects.

FIG. 5 is a bar graph which shows the percentage of time spent above pH 5.5 and 6.0 in each postprandial hour in the duodenum. Shaded bars represent data from healthy subjects and open bars represent data from cystic fibrosis patients. It is seen from this figure that an appropriate enteric coating for pancreatic enzyme therapy for cystic fibrosis patients would be dissolvable in the pH range of 4.5 through 5.5, and not 6 to 8 as is commonly used in commercial products.

Appropriate enteric coatings for the cystic fibrosis application include polyvinyl acetate phthalate, Colorcon, West Point, PA (pH 4.7); HP 50 (pH 5.0) and HP 55 (pH 5.5) which are produced by Shinetsu, Japan, and Eudragit 100 (pH 5.5) which is produced by Rohm Pharmaceuticals, Philadelphia, PA. Of course, blends of these coatings, or any other pharmaceutically acceptable coating with the proper dissolution characteristics can be used. It should be noted that the enteric coating adds minimally to the size and density parameters of the drug spherules.

In yet another illustrative embodiment of the invention, a radioactive marker for gastrointestinal transit studies is manufactured using nondigestible spheres of the appropriate diameter and density to achieve concomitant emptying. In a specific example, the spheres are radiolabeled with $^{99m}$Tc. The $^{99m}$Tc is mixed with about 2-3 ml of viscous, latex paint enamel. Spheres are rolled in this mixture to form a thin layer on the surface which is then dried prior to overcoating with a solution of 15% plexiglass in chloroform. The chloroform quickly evaporates, leaving a hard plexiglass coating. A similar procedure is used to radiolabel spheres with Indium. Markers manufactured according to the invention have the advantage of reliably tracking the flow of the solid portion of the meal and avoids the problem with labeling foodstuffs or live animals.

In addition, there are other conditions wherein the pH of the duodenum is known to be lower than normal, such as duodenal ulcers, Zollinger-Ellison Syndrome, alcoholism-created pancreatic insufficiency, to name just a few. Obviously, the active drug desired to be delivered would differ from the pancreatic enzyme embodiments described above, however, the principles of the invention can still be applied to achieve a customized drug for the pH profile and the gastric residence time desired for the treatment of the diseases.

In addition to the above-described uses of the dosage form of the instant invention, the principles of the invention can be applied to deliver drugs with saturable absorption slowly enough to maximize uptake, illustratively, iron, folate, β-Lactam antibiotics including amoxicillin, ampicillin, penicillin V, cephalexin, cephridrine, etc., angiotensin, converting enzyme inhibitors such as enalopril, captopril, vitamins, peptides, amino acids and related analogs. The dosage form can also be used to avoid gastric irritation by a drug such as aspirin, iron, and nonsteroidal anti-inflammatory drugs, such as indomethacin, etc.

The dosage form can additionally be used to provide delivery of drugs which are labile at gastric pH levels, illustratively erythromycin, penicillins, cephalosporins and other antibiotics.

Moreover, the low pH of the fed duodenum can be used to maximize the uptake of drugs with pH dependent absorption including, but not limited to, enalopril, methyldopa, ketoconazole, nonsteroidal anti-inflammatory drugs, such as indomethacin ibuprofen, mefanamic acid, naproxen, piroxicam, etc., chlorothiazide, and other diuretics, nalidixic acid and other urinary tract infection anti-infectives, cimetidine and other $H_2$-receptor antagonists, atenolol, timolol, propranolol, and other β-blockers, milrinone and other anti-hypertensive agents. In all of the uses of the dosage form, gastric degradation can be avoided by the appropriate choice of enteric coating.

Although the invention has been described in terms of specific embodiments and applications, persons skilled in the art in light of this teaching can generate additional embodiments without exceeding the scope or departing from the spirit of the claimed invention. Accordingly, it is to be understood that the drawings and descriptions in this disclosure are proffered to facilitate comprehension of the invention and should not be construed to limit the scope thereof.

What is claimed is:

1. A drug dosage system of the type wherein an active drug is administered orally to a living being so as to be transported by a chyme produced by the living being in response to an ingested meal, the chyme having a solid portion, the drug dose system comprising a multiplicity of subunits of the active drug, said subunits each having a substantially spherical configuration and a predeterminable density and diameter, said density and diameter being selectably related to one another in accordance with a relationship:

$$\left[ N_v = \frac{\Delta p * d_p^2}{\mu * <v>} \right]$$

$$N_v = \frac{g\Delta p * d_p^2}{\mu * <v>}$$

wherein $N_v$ is functionally related to the gastric residence time of said subunits relative to the liquid fraction of the meal, g is the gravitational constant, $\Delta p$ is the difference in density between said subunits and the chyme, $d_p$ is the diameter of said subunits, $\mu$ is the viscosity of the chyme, and $<v>$ is the linear velocity of the chyme; and
   wherein the value of $|\Delta p|*d_p^2$ is selected to achieve a predetermined rate of transport of said subunits and concomitant emptying thereof with the solid portion of the chyme.

2. The drug dosage system of claim 1 wherein said subunits are nondigestible and radiolabeled.

3. The drug dosage system of claim 1 wherein there is further provided an enteric coating for said subunits.

4. The drug dosage system of claim 1 wherein said density and diameter of said subunits are selected to achieve substantially concomitant emptying of said subunits and said chyme, whereby $|\Delta p|\cdot d_p^2$ has a value of between about 0 and 0.5.

5. The drug dosage system of claim 4 wherein said density of said subunits is approximately between 0.6 and 1.4 g/ml.

6. The drug dosage system of claim 5 wherein said diameter of said subunits is approximately between 0.5 mm and 2.0 mm.

7. The drug dosage system of claim 1 wherein the active drug is selected to be a digestive enzyme.

8. The drug dosage system of claim 7 wherein there is further provided an enteric coating for said subunits.

9. The drug dosage system of claim 8 wherein said enteric coating of said subunits is selected in response to predetermined gastrointestinal conditions.

10. The drug dosage system of claim 9 wherein said predetermined gastric condition is characterized by pancreatic insufficiency and said enteric coating is dissolvable in a pH range of approximately between 4.5 and 5.5.

11. The drug dosage system of claim 5 wherein there is further provided an alkaline component for increasing the pH of said subunits.

12. The drug dosage system of claim 11 wherein said alkaline component is sodium bicarbonate.

13. A drug dosage system of the type wherein an active drug is administered orally to a living being so as to be transported by a chyme produced by the living being in response to an ingested meal, the drug dose system comprising a multiplicity of subunits of the active drug, said subunits each having a substantially spherical configuration and a predeterminable density and diameter, said density and diameter being selectably related to one another in accordance with a relationship:

$$\left[ N_v = \frac{\Delta p * d_p^2}{\mu * <v>} \right]$$

$$N_v = \frac{g\Delta p * d_p^2}{\mu * <v>}$$

wherein $N_v$ is functionally related to the gastric residence time of said subunits relative to a liquid fraction of the meal, g is the gravitational constant, $\Delta p$ is the difference in density between said subunits and the chyme, $d_p$ is the diameter of said subunits, $\mu$ is the viscosity of the chyme, and $<v>$ is the linear velocity of the chyme; said density of the subunits being approximately between 0.6 and 1.4 g/ml; said diameter of said subunits being approximately between 0.5 and 2.0 mm; and $|\Delta p|*d_p^2$ having a value between about 0 and 0.5, whereby the subunits are transported in the living being at approximately the same rate of transport as a solid portion of a chyme.

14. The drug dosage system of claim 13 wherein said subunits are nondigestible and radiolabeled.

15. The drug dosage system of claim 13 wherein the active drug is a digestive enzyme.

16. The drug dosage system of claim 15 wherein there is further provided an enteric coating for said subunits.

17. The drug dosage system of claim 16 wherein said enteric coating is dissolvable in a pH range of approximately between 4.5 and 5.5.

18. The drug dosage system of claim 17 wherein there is further provided an alkaline component for increasing the pH of said subunits.

19. The drug dosage system of claim 18 wherein said alkaline component is sodium bicarbonate.

* * * * *